United States Patent
Kusakabe

(10) Patent No.: US 6,335,014 B1
(45) Date of Patent: Jan. 1, 2002

(54) MEDICAMENT FOR SUPPRESSING CANCER METASTASIS

(75) Inventor: Moriaki Kusakabe, 1-35-3, Kamikashiwada, Ushiku-shi, Ibarakiken 300-1232 (JP)

(73) Assignees: The Institute of Physical and Chemical Research, Saitama; Moriaki Kusakabe, Ibarakiken, both of (JP)

( * ) Notice: Subject to any disclaimer, the term of this patent is extended or adjusted under 35 U.S.C. 154(b) by 0 days.

(21) Appl. No.: 09/098,501

(22) Filed: Jun. 17, 1998

(51) Int. Cl.$^7$ .................. A61K 39/395; C12P 21/08
(52) U.S. Cl. .................. 424/155.1; 424/152.1; 424/145.1; 424/141.1; 424/130.1; 424/138.1; 424/172.1; 424/174.1; 530/388.24; 530/388.8; 530/388.85
(58) Field of Search .............. 530/388.1, 388.15, 530/388.23, 388.24, 388.8, 388.85, 387.1, 387.7, 389.1, 389.2, 389.7; 424/130.1, 138.1, 141.1, 142.1, 152.1, 155.1, 156.1, 172.1, 174.1, 145.1, 158.1

(56) References Cited

FOREIGN PATENT DOCUMENTS

WO    WO 92/07872    * 5/1992

OTHER PUBLICATIONS

Murphy–Ullrich, J.E. Anti–adhesive proteins of the extracellular matrix: Thrombospondin, tenascin, and SPARC. Trends in Glycoscience and Glycotechnology, 7: 89–100, Jul. 1995.*

Doi, D. et al. Immunohistochemical localization of tenascin, estrogen receptor and transforming growth factor–beta1 in human endometrial carcinoma. Gynecologic and Obstetric Investigation, 41: 61–66, 1996.*

Sakai, T. et al. Tenascin–C induction by the diffusible factor epidermal growth factor in stromal–epithelial interactions, J. Cellular Physiology, 165: 18–29, 1995.*

Sugawara, I. et al. Relationships among tenascin expression, DNA ploidy patterns, and multidrug resistance gene product (P–glycoprotein) in human colon carcinoma. Jpn. J. Cancer Res., 84:703–707, Jul. 1993.*

Deryugina, E.I. et al. Tenascin mediates human glioma cell migration and modulates cell migration on fibronectin. J. Cell Science., 109: 643–652, 1996.*

Derwent abstract of JP05111390A to Nippon Shinyaku Co Ltd, May 1993.*

Chiquet–Ehrismann, Cell, 47, pp. 131–139, 1986.

Erickson, Annu. Rev. Cell Biology, 5, pp. 71–92, 1989.

Sakakura, Tumer Matrix Biology, pp. 101–129, CRC Press, 1995.

Hiraiwa et al., J. Cell Science, 104, pp. 289–296, 1993.

Chiquet–Ehrismann et al., Cancer Research, 49, pp. 4322–4325, 1989.

Sakai et al., J. Cell Physiol., 165, pp. 18–29, 1995.

Shrestha et al., International Journal of Oncology, 8, pp. 741–755, 1996.

Oike et al., Int. J. Dev. Bio., 34, pp. 309–317, 1990.

Koyama et al., Histochem. Cell Biol., 106, pp. 263–273, 1996.

Saga et al., Gene & Development, 6, pp. 1821–1831, 1992.

English Language Abstract of JP 10–67799.

Kusakabe et al., Nyuugan Kiso Kenkyu, 5, pp. 41–45, 1996.

Abstracts of oral presentations in the 56th Annual Meeting of the Japanese Cancer Association in Kyoto, Japan in Sep. 1997 in Japanese Journal of Cancer Research, proceedings of the Japanese Cancer Association published Aug. 21, 1997, labeled IQO–03, KAO–02 and UAP–048.

* cited by examiner

*Primary Examiner*—Anthony C. Caputa
*Assistant Examiner*—Anne L. Holleran
(74) *Attorney, Agent, or Firm*—Greenblum & Bernstein, P.L.C.

(57) ABSTRACT

A cancer metastasis inhibitor which comprises as an active ingredient an anti-tenascin monoclonal antibody which neutralizes the physiological functions of a tenascin by binding to the FGF-like domain and other domains of the tenascin and prevents the metastasis of cancer to other organs such as the lungs.

6 Claims, No Drawings

MEDICAMENT FOR SUPPRESSING CANCER METASTASIS

TECHNICAL FIELD

This invention relates to a medicament that inhibits the metastasis of cancer cells. More specifically, it relates to a medicament which comprises a monoclonal antibody specific to tenascin as the effective ingredient and works as a cancer metastasis inhibitor.

BACKGROUND OF THE INVENTION

In the carcinogenesis of the epithelial cell, it is thought that the surrounding mesenchyme found around the epithelial cell (also known as the stroma), and in particular, the large molecular groups known as the extracellular matrix play a pivotal role. The extracellular matrix is an assembly that consists of various physiological substances such as collagens, and laminin and type IV collagen which compose the basement membrane, as well as tenascin, a glycoprotein with molecular weight of 190 and 250 kDa (Chiquet-Ehrismann, R., et al., Cell, 47, pp. 131–139, 1986).

Tenascin is found in the surrounding mesenchyme as a hexamer and is known to be expressed in a spatio-temporal manner in the processes of organogenesis, tissue regeneration, wound healing, and the proliferation or infiltration of cancer (Erickson, H. P., Annu.Rev. Cell Biol., 5, pp. 71–92, 1989; Sakakura, T., Tumor Matrix Biology, pp.101–129, CRC Press, 1995). With regards to the physiological function of tenascin, it is known to affect cell behavior in morphogenesis and tissue regeneration, including cell adhesion and detachment, the stimulation and inhibition of cell proliferation, as well as the activation of hemagglutination. Tenascin is ordinarily produced by fibroblasts, and it has been confirmed that cancer cells which are derived from the epithelium produce tenascin, the implication being that the production of tenascin in cancer cells is induced by a humoral factor deriving from the surrounding mesenchyme of cancer (Hiraiwa, N., et al., J. Cell. Science, 104, pp. 289–296, 1993). Furthermore, transforming growth factors (TGF β) and epidermal growth factors (EGF) are known as substances which induce and activate tenascin (Chiquet-Ehrismann, R., et al., Cancer Res., 49, pp. 4322–4325, 1989; Sakai, T., et al., J. Cell. Physiol., 165, pp. 18–29, 1995).

Regarding the role of tenascin in the proliferation and metastasis of cancer cells, it has been proven through experimentation with a tenascin-deficient mouse that the production of tenascin in cancer cells is regulated by an inducing factor deriving from the surrounding mesenchyme cells (Kusaksabe, et al., Nyuugan Kiso Kenkyu, 5, pp. 41–45, 1996). It has also been demonstrated that the expression of this inducing factor is dependent upon tenascin, in other words, that tenascin itself acts on the surrounding mesenchymal cells of cancer and promotes the production of this inducing factor. In this manner, the interactions between tenascin and the said inducing substance can be considered a type of signal transduction.

As described above, it has been implied that tenascin is involved in the tumor growth and metastasis of cancer cells however, an anticancer drug which targets tenascin is yet to be developed. Although attempts are being made to utilize anti-tenascin monoclonal antibodies for purposes of cancer treatment, there has been no report so far of attempts to inhibit the metastasis of cancer cells by obstructing the function of tenascin.

DISCLOSURE OF THE INVENTION

An object of the present invention is to provide a metastasis inhibitor for cancer cells. More specifically, the object of the present invention is to provide a cancer metastasis inhibitor that targets tenascin, a substance that influences the metastasis and proliferation of cancer cells.

As a result of extensive research to solve the aforementioned object, the inventors discovered that anti-tenascin monoclonal antibodies obstruct the process in which cancer cells that entered the blood stream adhere and grow in other tissues, and thereby inhibit the metastasis of cancer cells in a highly effective manner. The invention was completed on the basis of this knowledge.

The present invention thus provides a cancer metastasis inhibitor comprising as an active ingredient an anti-tenascin monoclonal antibody. The medicament of the present invention can be given to all mammals including humans for the purpose of preventing cancer metastasis, for example, to the lungs. In addition, the present invention also provides an inhibitor of cancer cell adhesion comprising an anti-tenascin monoclonal antibody.

According to another aspect, there are provided a method for inhibiting cancer metastasis which comprises the step of administering an effective amount of an anti-tenascin monoclonal antibody to a mammal including human; and a method for inhibiting the adhesion of cancer cells which comprises the step of administering an effective amount of an anti-tenascin monoclonal antibody to a mammal including human. According to further aspect, a use of the anti-tenascin monoclonal antibody for the manufacture of the above-mentioned medicament.

BEST MODE FOR CARRYING OUT THE INVENTION

The medicament of the present invention is characterized in that it comprises an anti-tenascin monoclonal antibody as an active ingredient and is used for the purpose of inhibiting cancer metastasis.

As for the anti-tenascin monoclonal antibody which is the active ingredient of the medicament of the present invention, it is preferred to use a monoclonal antibody that reacts specifically and substantially to tenascin. Among such monoclonal antibodies, it is desirable to use one that can obstruct the physiological functions of tenascin by bonding itself specifically to tenascin (i.e., a neutralizing antibody). Several varieties of tenascin isomers are known to exist, and a monoclonal antibody which reacts to any of these isomers, or alternatively, to multiple isomers can be used. The species of animal from which the monoclonal antibody will be developed are not particularly limited, and it is possible to use a facultative mammal that can be immunized by tenascin. Although there is no particular limitation to the subtype of monoclonal antibody, $IgG_{2a}$ κ, for example, is preferred.

In the case of administering the medicament of the present invention to humans, it is necessary to use, as the active ingredient, an anti-human tenascin monoclonal antibody that reacts to human derived tenascin. Such anti-human tenascin monoclonal antibodies may have cross-reactivity to non-human tenascin. For example, a monoclonal antibody that recognizes both mouse and human tenascin can be used as the active ingredient of the medicament of the present invention.

There is no particular limitation as to the epitope of a tenascin molecule that is recognized by the monoclonal antibody as being the active ingredient of the medicament of the present invention. For example, a monoclonal antibody which reacts to either one of the molecular domains of tenascin such as the EGF-like domain or fibronectin type III-like domain, or alternatively, to two or more domains can be used. Among these, though, the use of a monoclonal antibody which reacts to the EGF-like domain is preferred. Also, the monoclonal antibody may be modified with a single or more than two labeled compounds, or active ingredients for the treatment of cancer.

Examples of the anti-human tenascin monoclonal antibodies include, for example, 36-13-6 (A-D domain and fibronectin-like domain FN3-5; cross reacting to human and mouse; P. Shrestha, et al., International Journal of Oncology, 8, pp. 741–755, 1996; this antibody is also known as "DEAR2"), 7-13 (fibronectin type III-like domain; human-specific; P. Shrestha, et al., International Journal of Oncology, 8, pp. 741–755, 1996), 8C9 (EGF-like domain; human-specific; Oike, Y., et al., Int. J. Dev. Bio., 34, pp. 309–317, 1990; this antibody is also known as "RCB1"), 12-2-7 (EGF-like domain; cross reacting to human and mouse; Shrestha, P. et al., International Journal of Oncology, 8, pp.741–755, 1996), 3–58 (EGF-like domain; human-specific), and 3–6 (EGF-like domain; cross reacting to human and mouse; Koyama, Y., et al., Histochem. Cell Biol., 106, pp. 263–273, 1996; this antibody is also known as "DEAR1"). However, the monoclonal antibodies that can be used as the active ingredient of the medicament of the present invention are not limited to these examples (the information provided in brackets indicate the epitope of tenascin; these monoclonal antibodies all derive from rats). The tenascin used in developing anti-tenascin monoclonal antibodies can be easily obtained through the method described in literature (Oike, Y., et al., Int. J. Dev. Bio., 34, pp. 309–317, 1990).

The medicament of the present invention may preferably be administered parenterally. The form of preparation of the medicament of the present invention is not particularly limited; however, intravenous injections or intravenous drips are preferred. On occasion, intramuscular or hypodermic injections may be suitable. The medicament of the present invention may desirably be prepared in the form of a pharmaceutical composition comprising the active ingredient anti-tenascin monoclonal antibody, together with one or more pharmaceutical additives. More than two anti-tenascin monoclonal antibodies can be used in combination. The medicament of the present invention may be formulated together with one or more other ingredients effective for the therapeutic and/or preventive treatment of cancer, or the inhibition of metastasis.

The pharmaceutical additives used for the manufacture of the medicament of the present invention may be chosen by one of ordinary skilled in the art according to the type of the preparation. For example, stabilizers, solubilizing agents, buffering agents, pH modifiers, isotonicities, antiseptic substances or the like. The medicament can be manufactured as lyophilized injections or drip infusions. For the manufacture of such dry preparations, excipients may be used.

The medicament of the present invention can be administered to cancer hearing patients to prevent the metastasis of cancer. The medicament of the present invention functions to impede the process in which cells from cancer tissues enter the blood stream, adhere and grow in other tissues and form a metastasized lesion. There is no particular limitation to the type of metastasis, for example, to the lungs, liver, or bone. It is desirable that the dose is increased or decreased as necessary according to the purpose of administration, the conditions of the patient such as the weight and age, the type of the primary cancerous lesion, and severity of the cancer. In general, for an adult patient, it is desirable to administer a dose of approximately 1 to 1,000 mg either once a day or several times a day in divided doses. It is possible to administer intermittently at a rate of once in several days or several weeks.

EXAMPLES

The present invention will be explained in further detail with reference to examples as follows. However, the scope of the present invention is not limited to the examples provided below.

(1) Materials

A) Mouse Mammary Cancer Cell Line GLMT1

A spontaneously developed mammary cancer tissue was transplanted subcutaneously (dorsal skin) to a GRS/A strain mouse. One month later, the metastasized solid tumor which developed as a result of the cancer metastasizing to the lungs was harvested. This lung metastasized tumor was again transplanted subcutaneously to another mouse, and the solid tumor which metastasized and developed in the lungs was harvested. This operation was repeated 96 times after which mammary cancer cells taken from the lung metastasized lesion were placed under culture condition. Finally, a mammary cancer cell line, GLMT1, with highly lung-metastatic attributes was established. This GLMT1 cell does not produce tenascin in vitro, but had the ability to produce tenascin in vivo due to its dependence on the environment. In addition, the proliferation ability of this cell was not affected by the presence or absence of monoclonal antibodies given below (3-6, 36-13-6, and 8C9) that specifically recognize tenascin. Furthermore, there was no change observed in cell proliferation when stained with fluorescent dye (PKH).

B) Monoclonal Antibodies that Specifically Recognize Tenasin

For monoclonal antibodies that specifically recognize tenascin, the following monoclonal antibodies, produced according to the methods described in literature, were used.

a) Monoclonal antibody, 3-6 (Koyama, Y., et al., Histochem. Cell Biol., 106, pp. 263–273, 1996)

Cross reacting to human and mouse

Rat $IgG_{2a}$ κ

Recognition site: EGF-like domain of tenascin b) Monoclonal antibody, 36-13-6 (P. Shrestha, et al., International Journal of Oncology, 8, pp. 741–755, 1996)

Cross reacting to human and mouse

Rat $IgG_{2a}$ κ

Recognition site: A-D domain of tenascin c) Monoclonal antibody, 8C9 (Oike, Y., et al., Int. J. Dev. Bio., 34, pp. 309–317, 1990)

Human-specific

Rat $IgG_{2a}$ κ

Recognition site: EGF-like domain of tenascin d) Monoclonal antibody, 7-13 (P. Shrestha, et al., International Journal of Oncology, 8, pp. 741–755, 1996)

Human-specific

Rat $IgG_{2a}$ κ

Recognition site: fibronectin type III-like domain

C) Tenascin Knockout Mouse

The tenascin knockout mouse was prepared according to the method described in literature (Saga, Y., et al., Gene, Dev., 6, pp. 1821–1831, 1992), and a tenascin knockout congenic GRS/A mouse strain was prepared by backcross mating to a GRS/A inbred strain.

D) Deposit of Mouse-Rat Hybridoma 3-6

On Apr. 27, 2001, a deposit of mouse-rat hybridoma 3-6 was made to the International Patent Organism Depositary, National Institute of Advanced Industrial Science and Technology, AIST Tsukuba Central 6, 1-1 Higashi 1-chome, Tsukuba-shi, Ibaraki-ken, 305–8566, Japan under the Budapest Treaty. The depositary ID of the deposit is FERM BP-7574.

(2) Methods and Results

A) Experimental Lung Metastasis Using Mouse Mammary Cancer Cell Line (GLMT1

After trypsinization of GLMT1 cells and rinsing, the cell surface was stained with fluorescent dye (PKH26). The fluorescent dye of stained cells that had been counted to a known number was extracted using isopropanol. The absorbance (553 nm) was determined, and a standard curve was made on the basis of the correlation between the number of cells and absorbance of fluorescence dye. At the same time, GLMT1 cells were inoculated (injected intravenously: $1 \times 10^6$ cells) into GRS/A inbred mice or tenascin knockout congenic GRS/A mice (TN congenic mouse). The lungs were dissected 7 days later and perfused with saline in order to wash out blood cells and cancer cells that had not adhered and grown in the lungs. The lungs were minced and placed in isopropanol for 2 hours at room temperature to extract fluorescent dye from cancer cells adhered and grown in the lungs. After removing the cells by centrifugation, the absorbance of fluorescent dye in the supernatant was measured and the number of cancer cells which had adhered and grown in the lungs was determined on the basis of a standard curve. Using this methodology, the total number of metastasizing cells in the lungs can be measured with accuracy. The results are provided in Table 1 (the numbers given in the table indicate the number of cells).

In the group of NM (normal male mouse), $9 \times 10^6$ cells had metastasized to the lung (adhesion to the lung) on the first day, but the adhered and grown cells had decreased in number to $5 \times 10^6$ cells by the third day. On the fifth and seventh days the adhered and grown cells had again increased in number to $4.0 \times 10^6$ cells and $5.5 \times 10^6$ cells respectively; however, this can be explained by the phenomenon where cancer cells in the blood which circulate through the body gradually adhere and grow in the lungs. In the group of NF (normal female mouse), the number of adhered and grown cells on the first day was lower in comparison with that in the male mouse, and an increase in number of adhered and grown cells between the third and seventh day was barely observed. This may be accounted by the fact that GLMT1 cells react to the female hormone (estrogen) when tenascin is present in the body and are stimulated to produce a smaller-form tenascin (one of the isoforms). This small-form tenascin acts to inhibit cell proliferation; as a result, the proliferation of GLMT1 cells is suppressed and thus it can be considered that the rise in the number of adhered and grown cells was inhibited.

In the groups of KOM (tenascin knockout male mouse) and KOF (tenascin knockout female mouse), both had lower adherent and growth rates compared to that in the group of normal male mouse. This may be explained by the fact that there is no production of tenascin in the tenascin knockout mouse, and accordingly, no production of tenascin-inducing factors (the Japanese patent unexamined publication (KOKAI) No.(Hei)10-67799/1998). The cancer cell itself cannot produce sufficient tenascin in vivo, lowering the growth level of the cancer cell itself. The similarity of the adherent and growth rate in KOF to KOM can be explained by the fact that no tenascin is produced in vivo in the group of KOF; thus, cancer cells are unaffected by estrogen even in the presence of estrogen.

TABLE 1

| Day | NM | NF | KOM | KOF |
|---|---|---|---|---|
| 1 | 90,000 | 55,000 | 60,000 | 72,000 |
| 3 | 26,000 | 41,000 | 13,000 | 9,000 |
| 5 | 42,000 | 43,000 | 15,000 | 15,000 |
| 7 | 55,000 | 44,000 | 29,000 | 35,000 |

In the experiment above, the monoclonal antibody 3-6 (i.p.) that is specific in was administered by injection three days after the cancer cell was inoculated. Further, on the basis of the results obtained from the above experiment, the effect of the monoclonal antibody in metastasis inhibition was determined five days after the cancer cell was inoculated. With a dose of 100 µg, 250 µg, and 500 µg (per mouse), the metastasis of cancer cells to the lungs was inhibited in a dose dependent manner (control group: 56,000 cells; 100 µg: 47,000 cells; 250 µg: 33,000 cells; 500 µg: 17,000 cells). When the dose was increased from 500 µg to 1,000 µg, further inhibition of the number of adhered and grown cells was not observed (1,000 µg: 16,000 cells). This may indicate the influences of factors other than tenascin. Based on these results the following experiment was conducted using a dosage of 250 µg per mouse.

GLMT1 cells were injected intravenously ($1 \times 10^6$ cells) in a similar manner, and three days later the anti-tenascin antibody 3-6 or 36-13-6 was administered by intraperitoneal injection. In a normal mouse, the adherence and growth of GLMT1 in the lungs was significantly inhibited in comparison with the control group, and this tendency was particularly marked in the case of 3-6 (Table 2). On the other hand, in the group of mice that had been administered with 8C9 which specifically recognizes human tenascin (but not mouse tenascin), there was no significant difference in the rate of adherence and growth of GLMT1 in comparison with the control group. This may be explained by the fact that 8C9 cannot act as a neutralizing antibody against tenascin produced by the host mouse or by GLMT1 itself, and thus cannot inhibit the adherence and growth of GLMT1 to the lungs.

While, among the groups of tenascin knockout mice administered with the monoclonal antibody, there was no significant difference from the controlled. This result indicates that GLMT1 could not produce tenascin in vivo either, and tenascin production by GLMT1 may have been suppressed as a result of a deficiency in some form of tenascin inducing factors in the tenascin knockout mouse.

TABLE 2

| experimental group | control | 3-6 | 36-13-6 | 8C9 |
|---|---|---|---|---|
| normal mouse | 53,000 | 15,000 | 27,000 | 52,000 |
| knockout | 29,000 | 27,000 | 27,000 | 28,000 |

In addition, when $2 \times 10^6$ cells were inoculated subcutaneously in the dorsal skin of the mice, the monoclonal antibody 3-6 had completely inhibited metastasis (metastasis was completely inhibited in five mice, and the mean tumor weight was 0.36 g), and the monoclonal antibody 36-13-6 had significantly controlled metastasis (metastasis was observed in two out of seven mice, the mean tumor weight being 0.42 g). Among the control mice, metastasis was identified in all six mice (the mean tumor weight was 0.76 g). As the epitope for 3-6 is identified in the EGE-like repeat domain, cellular adhesion relating to cancer cell metastasis may be regulated by the EGF-like domain, and 3-6 appears to inhibit lung metastasis of GLMT1 due to its function as a neutralizing antibody to the EGF-like functions of tenascin.

B) Metastasis Experimentation Using Human Cancer Cells

Human cancer cell lines A431 (human stratified epithelial carcinoma cell: does not express tenascin in vitro) and A375 (human melanoma cell: expresses tenascin in vitro) were inoculated subcutaneously in the dorsal skin ($2\times10^6$ cells) or injected intravenously ($1\times10^6$ cells) to a nude mouse. The anti-tenascin monoclonal antibody (250 $\mu$g) was then administered in the same method as described above, after which the tumor weight and the number of cancer cells that metastasized to the lungs were determined. The results are shown below (the percentages given in Table 3 indicate the tumor suppressing rate calculated on the basis of the difference in weight of the tumors; the percentages given in Table 4 show the adherence and growth rate in the lungs on day 7). These results clearly show that in experiments where human cancer cells were used, the antibodies which recognize EGF-like domains demonstrated a high inhibitory effect on tumor growth, and significantly inhibited cancer cell metastasis to the lungs (adhering to the lungs).

TABLE 3

| antibody administered | A431 | A375 |
|---|---|---|
| control | 0% | 0% |
| 8C9 | 80% | 83% |
| 7-13 | 63% | 57% |
| 36-13-6 | 62% | 59% |

TABLE 4

| antibody administered | A431 | A375 |
|---|---|---|
| control | 100% | 100% |
| 3-6 | 73% | 75% |

What is claimed is:

1. A method for inhibiting cancer metastasis which comprises administering therapeutically effective amount of an anti-tenascin monoclonal antibody to a cancer bearing patient, wherein the anti-tenascin monoclonal antibody recognizes an EGF-like domain of a tenascin.

2. The method according to claim 1, wherein the anti-tenascin monoclonal antibody is monoclonal antibody 3-6.

3. The method according to claim 1, wherein the metastasis takes place in the lungs.

4. A method for inhibiting cancer cell attachment and growth which comprises administering a therapeutically effective amount of an anti-tenascin monoclonal antibody to a cancer bearing patient in order to inhibit cancer cell attachment and growth, wherein the anti-tenascin monoclonal antibody recognizes an EGF-like domain of a tenascin.

5. The method according to claim 4, wherein the anti-tenascin monoclonal antibody is monoclonal antibody 3-6.

6. The method according to claim 4, wherein the inhibiting cancer cell attachment and growth takes place in the lung.

* * * * *

UNITED STATES PATENT AND TRADEMARK OFFICE
CERTIFICATE OF CORRECTION

PATENT NO. : 6,335,014 B1
DATED : January 1, 2002
INVENTOR(S) : M. Kusakabe

It is certified that error appears in the above-identified patent and that said Letters Patent is hereby corrected as shown below:

Title page,
Item [56], References Cited, U.S. PATENT DOCUMENTS, the following was omitted and should be included:
-- 5,417,209    5/23/95    Morrison, John C.    128/645 --
OTHER PUBLICATIONS, the following was omitted and should be included:
-- Natali, P.G. et al. Comparative analysis of the expression of the extracellular matrix protein tenascin in normal human fetal, adult and tumor tissues. Int. J. Cancer, 47:811-816, 1991. --
Item [57], ABSTRACT,
Line 4, "FGF" should be -- EGF --.

Column 8,
Line 11, after "administering" insert -- a --.

Signed and Sealed this

Twenty-second Day of October, 2002

*Attest:*

*Attesting Officer*

JAMES E. ROGAN
*Director of the United States Patent and Trademark Office*